United States Patent [19]

Pearson et al.

[11] Patent Number: 5,232,424
[45] Date of Patent: Aug. 3, 1993

[54] BACK AND STOMACH SUPPORT DEVICE

[76] Inventors: David P. Pearson, 861 Boxthorn Ave., Newbury Park, Calif. 91320; Thomas J. Johnston, 24 Thunder Trail, Irvine, Calif. 92714

[21] Appl. No.: 755,995

[22] Filed: Sep. 6, 1991

[51] Int. Cl.⁵ .............................. A63B 21/072
[52] U.S. Cl. ........................ 482/106; 602/19; 2/338
[58] Field of Search ............ 482/106; 602/19; 128/95.1, 96.1; 2/321, 338

[56] References Cited

U.S. PATENT DOCUMENTS

| | | | |
|---|---|---|---|
| 3,038,166 | 6/1962 | Tobias | 2/321 X |
| 3,105,974 | 10/1963 | De Grazia | 2/338 X |
| 3,420,230 | 1/1969 | Ballard | 602/19 X |
| 4,384,372 | 5/1983 | Rector | 602/19 X |
| 4,413,358 | 11/1983 | Timenez | 2/321 |
| 4,459,979 | 7/1984 | Lewis, Jr. | 602/19 |
| 4,508,110 | 4/1985 | Modglin | 602/19 |
| 4,545,370 | 10/1985 | Welsh | 602/19 |
| 4,648,390 | 3/1987 | Friddle | 602/19 |
| 4,685,668 | 8/1987 | Newlin, Jr. | 2/338 X |
| 4,745,911 | 5/1988 | Bender | 602/19 X |
| 4,782,535 | 11/1988 | Yewer, Jr. et al. | 2/321 |
| 4,802,667 | 2/1989 | Altner | 2/338 X |
| 4,867,145 | 9/1989 | Goth | 128/96.1 |
| 4,905,993 | 3/1990 | Barode | 2/338 X |
| 4,964,401 | 10/1990 | Taigen | 602/19 X |
| 4,968,027 | 11/1990 | Anderson | 2/338 X |
| 4,991,573 | 2/1991 | Miller | 602/19 |
| 5,040,524 | 8/1991 | Votel et al. | 128/95.1 X |
| 5,046,488 | 9/1991 | Schiek, Sr. | 602/19 |
| 5,065,773 | 11/1991 | Jackson et al. | 2/338 X |
| 5,070,866 | 12/1991 | Alexander et al. | 602/19 |

Primary Examiner—Robert Bahr
Attorney, Agent, or Firm—John J. Posta, Jr.

[57] ABSTRACT

The back and stomach support device is utilizable by weightlifters, stevedors, etc., and includes an elongated flexible back strap with a resilient, flexible back cushion attached to the inner surface thereof. The back strap extends forwardly at the sides of the device and ends in opposed front loops through which the opposite ends of a front belt extend. To the inner surface of the front belt is connected a resilient, flexible stomach cushion. The front belt can be cinched tight by means of its opposite ends and be releasably held in place for example by hook-bearing strips and hook-receiving strips on the belt. The device encircles the waist and effectively supports both back and stomach to prevent muscle strain. The strap and belt are shorter in height than the cushions so that no pinching of the skin occurs during tightening. The opposite ends of the cushions may be tapered down for a similar reason and the cushions are short enough not to intercept each other. Preferably, they are of flexible foamed plastic, while the belt and strap are preferably of unfoamed flexible plastic. Detachable shoulder suspenders may be connected to the cushions and/or strap and belt to hold the device loosely in place when not needed.

9 Claims, 2 Drawing Sheets

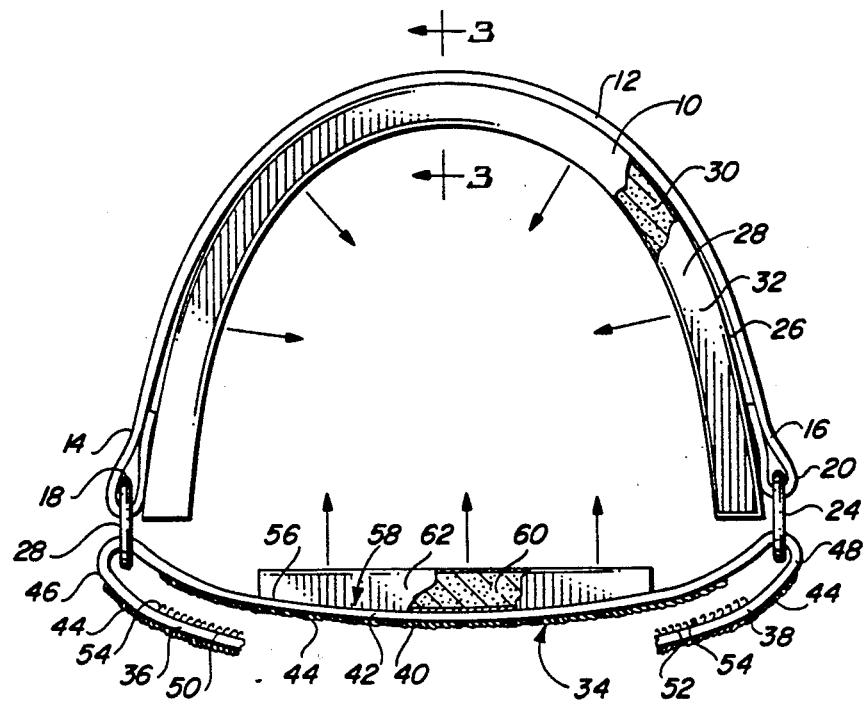

BACK AND STOMACH SUPPORT DEVICE

BACKGROUND OF THE INVENTION

1. Field of the Invention

The present invention generally relates to weightlifting protectors and more particularly to an improved back and stomach support device for weightlifters.

2. Prior Art

Various protective belts have been devised to help support the back and stomach of weightlifters, stevedores and the like in order to prevent strains and damage to muscles, soft internal organs, cartilage, and the spinal column and other bones during lifting of heavy weights such as are encountered by professional and amateur weightlifters, movers, stevedores, etc.

Thus, U.S. Pat. No. 4,964,401 discloses a belt with a rubber core in which is embedded an inflexible rigid strip. The core is backed by a strap of equal height, and the belt is releasably secured in front by overlapping opposed VELCRO brand hooks and receptors. In one embodiment a buckle is provided to help cinch the belt. This belt has certain disadvantages: (1) the inflexible strip in the core makes close fitting of the belt to the body difficult and/or painful; (2) since the core and backing strap are of the same height, they can dig in and pinch the skin during tightening of the belt; (3) moreover, the means of tightening the belt is merely by overlapping its two ends or also using a single front buckle, so that close cinching and proper centering of the belt may be difficult. U.S. Pat. No. 4,685,668 discloses a weightlifting belt with similar difficulties.

There remains a need for an improved, inexpensive, durable weightlifting belt which will efficiently protect the weightlifter against muscle strain and damage the soft internal organs, cartilage and bones. The device should be easy to don and to center properly and should not pinch the skin, even when cinched tight. Preferably, the device can be left loosely in place without falling off.

SUMMARY OF THE INVENTION

The improved back and stomach protective device of the present invention satisfies all the foregoing needs. The device is substantially as set forth in the Abstract of the Disclosure.

Thus, the device comprises a flexible, resilient back strap preferably of nylon or the like plastic webbing on the inner surface of which is connected a flexible, resilient back cushion, for example, foamed rubber or plastic, which is of greater height, thickness and length than the strap. The strap is centered on the cushion.

The opposite front ends of the strap terminate in connector loops through which the opposite ends of a flexible, resilient front belt preferably of nylon or the like plastic webbing are passed and then lapped back over the remainder of the belt or themselves, being releasably held in place by hook and receptor-type fasteners on the belt, or by other means.

Thus, the belt can be cinched from opposite ends to center it. It bears centered on the inner surface thereof a flexible, resilient stomach cushion, for example, of foamed plastic or rubber of greater height and thickness, but of shorter length than the belt. The two cushions are positioned and dimensioned so that they do not intersect when the device is cinched tight. Preferably, the opposite ends of the cushions are tapered down to prevent skin pinching during tightening of the device. That is also the reason for the cushions being of greater than the strap and belt and being centered relative thereto. As tightening of the device takes place, the strap and belt press the cushions against the waist flesh and the cushions arc outwardly around the strap and belt, allowing room for the flesh and preventing skin pinch.

The device is simple, durable, inexpensive and efficient, being comfortable to wear. It can include a pair of shoulder suspenders attached to the cushions and/or strap and belt so that it can be held loosely in place when not in use. Various other features of the device of the present invention are set forth in the following detailed description and accompanying drawings.

DRAWINGS

FIG. 1 is a schematic, fragmentary top plan view, partly broken away, of a first preferred embodiment of the improved back and stomach support device of the present invention;

FIG. 2 is a schematic, fragmentary enlarged top plan view of the overlapped portions of the front belt of the device of FIG. 1;

FIG. 3 is an enlarged schematic section of the back cushion and strap of FIG. 1, taken along the section line A—A of FIG. 1, shown with the back cushion and strap in repose;

FIG. 4 is an enlarged schematic section of the back cushion and strap of FIG. 1, taken along the section line A—A of FIG. 1, shown with the back cushion and strap under cinching force;

DETAILED DESCRIPTION

Figures 1-4

Figure 5:
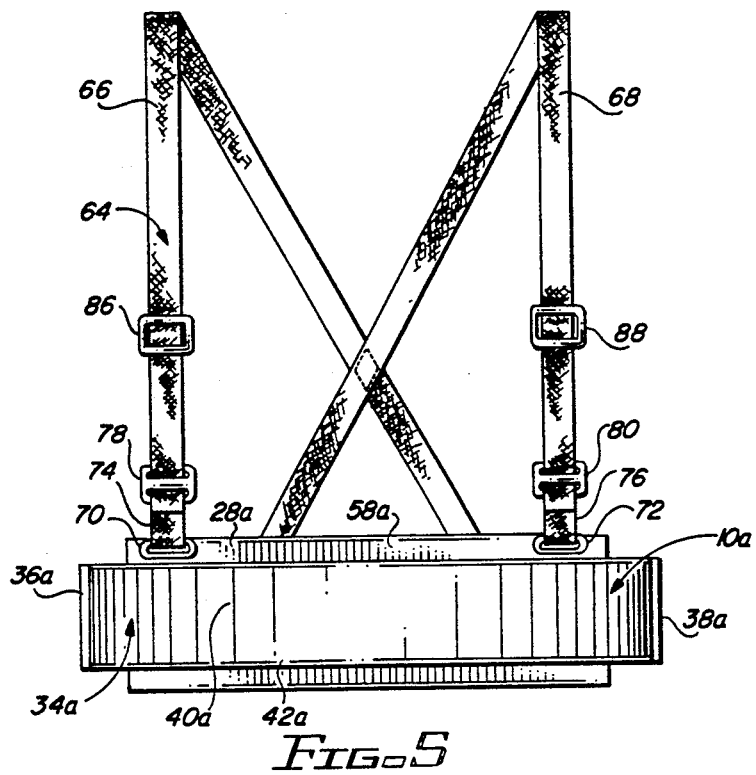
FIG. 5 is a schematic front elevation of a second preferred embodiment of the improved back and stomach support device of the present invention.

Now referring more particularly to FIGS. 1-4 of the drawings, a first preferred embodiment of the improved back and stomach support device of the present invention is schematically depicted therein. Thus, device 10 is shown, which comprises an elongated, flexible, resilient back strap 12, for example, of leather or of natural or synthetic cloth webbing such as nylon and of any suitable thickness, height and length, e.g., about 1/16" thick nylon webbing about 3" in height and 18-20" in length, extending around the rear of device 10 and with its two opposite ends terminating at the front sides of device 10 in loops 18 and 20, respectively, bearing connector rings 22 and 24, respectively.

To the inner surface 26 of strap 12 is connected, as by stitching or the like (not shown) a flexible, resilient self-supporting back cushion 28 having a core 30, for example, of foamed rubber or plastic or the like wrapped in cloth 32. Each cushion 28 may be, for example, of about equal or slightly greater length (such as 20") than back strap 12, and is of greater height and thickness than strap 12. For example, cushion 28 may be about 5" in height and about ½" in thickness and strap 12 is centered thereon so that cushion 28 extends above and below strap 12, as shown in FIGS. 3 & 4, preventing skin pinch as device 10 is tightened around the waist of the weightlifter. From FIGS. 3 and 4, it will be noted that in repose strap 12 and cushion 28 are vertical, but that as device 12 is tightened cushion 28 bows outwardly above and below strap 12 allowing room for waist skin.

Device 10 also includes an elongated, flexible, resilient front belt 34, for example, of leather or of cloth of natural or synthetic material such as nylon. Preferably, belt 34 is similar to strap 12 in height and thickness. It may be, for example, about 32"-52" in length or more, with the opposite ends 36 and 38 thereof passing through rings 22 and 24, respectively, and overlapping part of the remainder of belt 34, as shown in FIG. 1.

The front surface 40 of the central portion 42 of belt 34 bears hook-receiving-type receptors 44, as do surfaces 46 and 48, respectively, of ends 36 and 38, respectively, while the opposite surfaces 50 and 52 of ends 36 and 38 bear hooks 54. Thus, hooks 54 can releasably adhere ends 36 and 38 in any desired position to portion 42 (FIG. 1) or to each other (FIG. 2).

The rear surface 56 of central portion 42 of front belt 34 has connected thereto, as by stitching or the like (not shown), a flexible, resilient stomach cushion 58, which may, for example, comprise a foamed rubber or plastic core 60 wrapped in a cloth covering 62. Cushion 58 is of shorter length than front belt 34. Thus, it may be, for example, about 12-14" in length of a greater height than belt 34, for example, about 4-5" as opposed to about 3" for belt 34, and of a greater thickness, for example, about ⅛", as opposed to about 1/16" for belt 34. Cushion 58 is centered on belt 34, secured thereto and extends above and below belt 34. It prevents skin pinching during tightening of device 10, in the same manner as does back cushion 28 (FIGS. 3 & 4).

Both back cushion 28 and stomach cushion 58 are uniformly flexible and resilient, containing no inflexible components, so that they cannot injure the user, but can properly conform to waist contours. Device 10 is light in weight, inexpensive and durable and is highly effective in preventing strain and injury to the weightlifter. Cinching of device 10 can be carried out so that it occurs simultaneously at both ends 36 and 38, so that cushions 28 and 58 will remain properly centered for maximum protection of the weightlifter.

Figures 5 and 6

Figure 6:
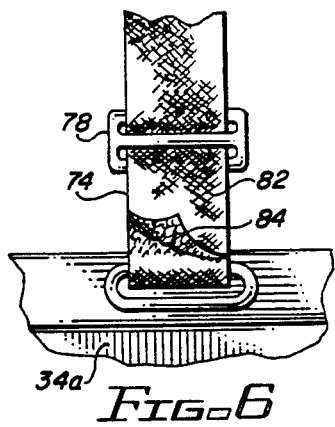
FIG. 6 is an enlarged, schematic, fragmentary front elevation of the releasable suspender-connecting means of the device of FIG. 5; and, FIG. 7 is a schematic top plan view, partly broken away, of a third preferred embodiment of the improved back and stomach support device of the present invention.

Now referring more particularly to FIGS. 5 and 6, a second preferred embodiment of the improved back and stomach support device of the present invention is schematically depicted therein. Thus, device 10a is shown. Components thereof similar to those of device 10 bear the same numerals but are succeeded by the letter "a".

Device 10a is identical to device 10, except as follows:

Device 10a includes shoulder suspenders 64 comprising shoulder straps 66 and 68 crossed in the rear. Straps 66 and 68 are connected directly, as by sewing, to back cushion 28a and are also connected at the front thereof to cushion 58a by means of slots 70 and 72 in the upper end of cushion 58a. In this regard, cloth strips 74 and 76 pass thru slots 70 and 72, respectively, and through rings 78 and 80. Strips 74 and 76 have hook-receiving receptors 82 on one surface and hooks 84 on an opposing surface to releasably connect strips 74 and 76 into openable loops. Strips 74 and 76 are trained around rings 78 and 80, respectively, as are the looped lower ends of strips 66 and 68.

Suspenders 64 can be released from cushions 28a and 58a merely by opening strips 74 and 76. The length of straps 66 and 68 can be adjusted through conventional cinch buckles around which straps 66 and 68 are looped.

Suspenders 64 allow device 10a to be worn loosely, for comforts sake, with front belt 34a uncinched until it is desired to use device 10a during weightlifting. Thus, suspenders 64 are a great convenience. Suspenders 64 can be removed from device 10a for repair, replacement, or when device 10a is to be used in competition. The other advantages of device 10a are similar to those of device 10.

Figure 7

Figure 7:
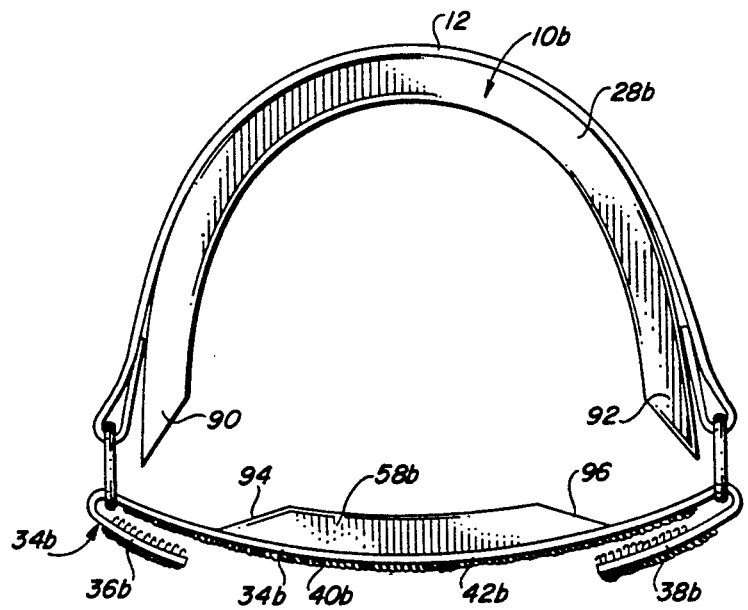

A third preferred embodiment of the present device is schematically depicted in FIG. 7. Thus, device 10b is shown. Components thereof similar to those of device 10 bear the same numerals but are succeeded by the letter "b".

Device 10b is identical to device 10, except as follows:

a) The opposite ends 90 and 92 of cushion 28b are tapered down forwardly and outwardly to eliminate the possibility of skin pinch during cinching device 10b;

b) The opposite ends 94 and 96 of cushion 58b are tapered down forwardly and outwardly for the same reasons; and, c) The velcroed ends 36b and 38b of front belt 34b are short and releasably connectable only to the velcroed front surface 40b of portion 42b of belt 34b.

Device 10b has the other advantages of device 10.

Various modifications, changes, alterations and additions can be made in the improved device of the present invention, its components and parameters. All such modifications, changes, alterations and additions as are within the scope of the appended claims form part of the present invention.

What is claimed is:

1. An improved back and stomach support device, said device comprising, in combination:
  a) an elongated, flexible, resilient back strap having an outer surface and an inner surface, said strap having a pair of opposed front ends;
  b) an elongated, flexible, resilient back cushion having opposed front ends, said back cushion being of greater height, thickness and length than said strap, and connected to the inside of said strap;
  c) loop connector means connected to the front ends of said strap;
  d) an elongated, flexible, resilient front belt having opposite ends of front and back sides, said opposite ends passing through said connector means being looped thereover and being releasably adjustably secured to said front belt to adjust the circumference of said device; and,
  e) an elongated, flexible, resilient stomach cushion having opposite ends, said stomach cushion being of greater height and thickness but of shorter length than said belt and being connected to the back side of said belt.

2. The improved support device of claim 1 wherein said front ends of said back cushion taper down in thickness to prevent skin pinch during tightening of said device.

3. The improved support device of claim 1 wherein said opposite ends of said stomach cushion taper down in thickness to prevent skin pinch during tightening of said device.

4. The improved support device of claim 1 wherein said stomach cushion and said back cushion are sufficiently short in length so as not to intercept each other during tightening of said device, thereby preventing skin pinching.

5. The improved support device of claim 1 wherein said belt opposite ends bear hook-receiving receptors on one side thereof and hooks on the other side thereof, whereby said belt ends can be releasably attached to each other.

6. The improved support device of claim 1 wherein said opposite ends of said belt and the front side of the remainder of said belt bear mating hook and receiving means, whereby said opposite ends of said belt are releasably securable, after cinching said device, to said remainder of said belt.

7. The improved support device of claim 1 wherein said device includes adjustable shoulder suspenders connected at the rear thereof to one of said back strap and back cushion and at the front thereof to one of said belt and stomach cushion to releasably hold said cushions in place when said belt is uncinched.

8. The improved support device of claim 7 wherein said suspenders are releasably secured to the remainder of said device by hook and receptor means.

9. The improved support device of claim 1 wherein said cushions comprise foamed plastic or rubber and said belt and strap comprise plastic webbing.

* * * * *